(12) United States Patent
Pietsch et al.

(10) Patent No.: US 11,557,385 B2
(45) Date of Patent: Jan. 17, 2023

(54) MOBILE DATA APPLIANCE FOR CHECKING MEDICATION

(71) Applicants: Wolf-Ruediger Pietsch, Hoevelhof (DE); Manfred Kesselmeier, Paderborn (DE); Philipp Hoffmann, Paderborn (DE)

(72) Inventors: Wolf-Ruediger Pietsch, Hoevelhof (DE); Manfred Kesselmeier, Paderborn (DE); Philipp Hoffmann, Paderborn (DE)

( * ) Notice: Subject to any disclaimer, the term of this patent is extended or adjusted under 35 U.S.C. 154(b) by 616 days.

(21) Appl. No.: 16/500,476

(22) PCT Filed: Feb. 28, 2018

(86) PCT No.: PCT/DE2018/100172
§ 371 (c)(1),
(2) Date: Oct. 3, 2019

(87) PCT Pub. No.: WO2018/184624
PCT Pub. Date: Oct. 11, 2018

(65) Prior Publication Data
US 2020/0188234 A1  Jun. 18, 2020

(30) Foreign Application Priority Data

Apr. 6, 2017   (DE) ...................... 20 2017 102 033.9
Nov. 20, 2017  (EP) ...................................... 17202491

(51) Int. Cl.
  *B65D 81/24*    (2006.01)
  *G16H 20/10*    (2018.01)
  (Continued)

(52) U.S. Cl.
  CPC ............ *G16H 20/10* (2018.01); *A61J 7/0418* (2015.05); *A61J 7/0427* (2015.05); *A61J 7/0454* (2015.05);
  (Continued)

(58) Field of Classification Search
  CPC ........ G16H 20/10; G16H 10/60; G16H 20/13; G16H 40/67; A61J 7/0418; A61J 7/0427; A61J 7/0454; A61J 7/0481; Y02A 90/10
  (Continued)

(56) References Cited

U.S. PATENT DOCUMENTS 5,157,640 A * 10/1992 Backner ................. G04G 11/00
                                                    368/41
6,075,755 A *  6/2000 Zarchan ................. G16H 10/65
                                                    368/10

(Continued)

FOREIGN PATENT DOCUMENTS

DE           29712539 U1    10/1997
DE       202012000410 U1     2/2012

OTHER PUBLICATIONS

English translation of International Preliminary Report on Patentability dated Oct. 17, 2019, in International Application No. PCT/DE2018/100172.

(Continued)

*Primary Examiner* — Tai T Nguyen
(74) *Attorney, Agent, or Firm* — Patent Central LLC; Stephan A. Pendorf

(57) ABSTRACT

A mobile data appliance for reminding patients to take medicaments and the like, including a power supply unit, a computing unit for processing medication data, a storage unit for storing the medication data, a display unit for representing medication data, a signal-transmitting unit for emitting a reminder signal for taking medicaments, and an interface unit for external data exchange. The storage unit includes a medication plan memory in which medication data produced by an authorized body is stored. A medication plan program is provided, by means of which time-dependent and/or location-dependent medication data is read out (Continued)

of the medication plan memory store, and viewed on the display unit and/or the reminder signal is emitted by means of the signal emitter unit.

8 Claims, 1 Drawing Sheet

(51) Int. Cl.
*A61J 7/04* (2006.01)
*G16H 40/67* (2018.01)
*G16H 10/60* (2018.01)
*G16H 20/13* (2018.01)

(52) U.S. Cl.
CPC ............ *A61J 7/0481* (2013.01); *G16H 10/60* (2018.01); *G16H 20/13* (2018.01); *G16H 40/67* (2018.01)

(58) Field of Classification Search
USPC ........................................................ 206/438
See application file for complete search history.

(56) References Cited

U.S. PATENT DOCUMENTS

| | | | |
|---|---|---|---|
| 10,352,759 B1 * | 7/2019 | Jensen | A47G 23/12 |
| 10,561,363 B1 * | 2/2020 | Florissant | A61B 5/02233 |
| 2009/0009470 A1 * | 1/2009 | Choi | G04G 21/00 |
| | | | 345/158 |
| 2016/0161985 A1 | 6/2016 | Zhang | |
| 2019/0267125 A1 * | 8/2019 | Benzel | G16H 20/10 |

OTHER PUBLICATIONS

International Search Report dated Jul. 3, 2018, in International Application No. PCT/DE2018/100172.
Anonymous: "My KP Meds", Apr. 30, 2016 (Apr. 30, 2016), Kaiser Permanente, Retrieved from the Internet: https://mydoctor.kaiserpemnanente.org/mas/mapmg/member_tools/managing_care/MyKPMeds.html (retrieved on Jun. 6, 2018), XP002781695, pp. 1-3.

* cited by examiner

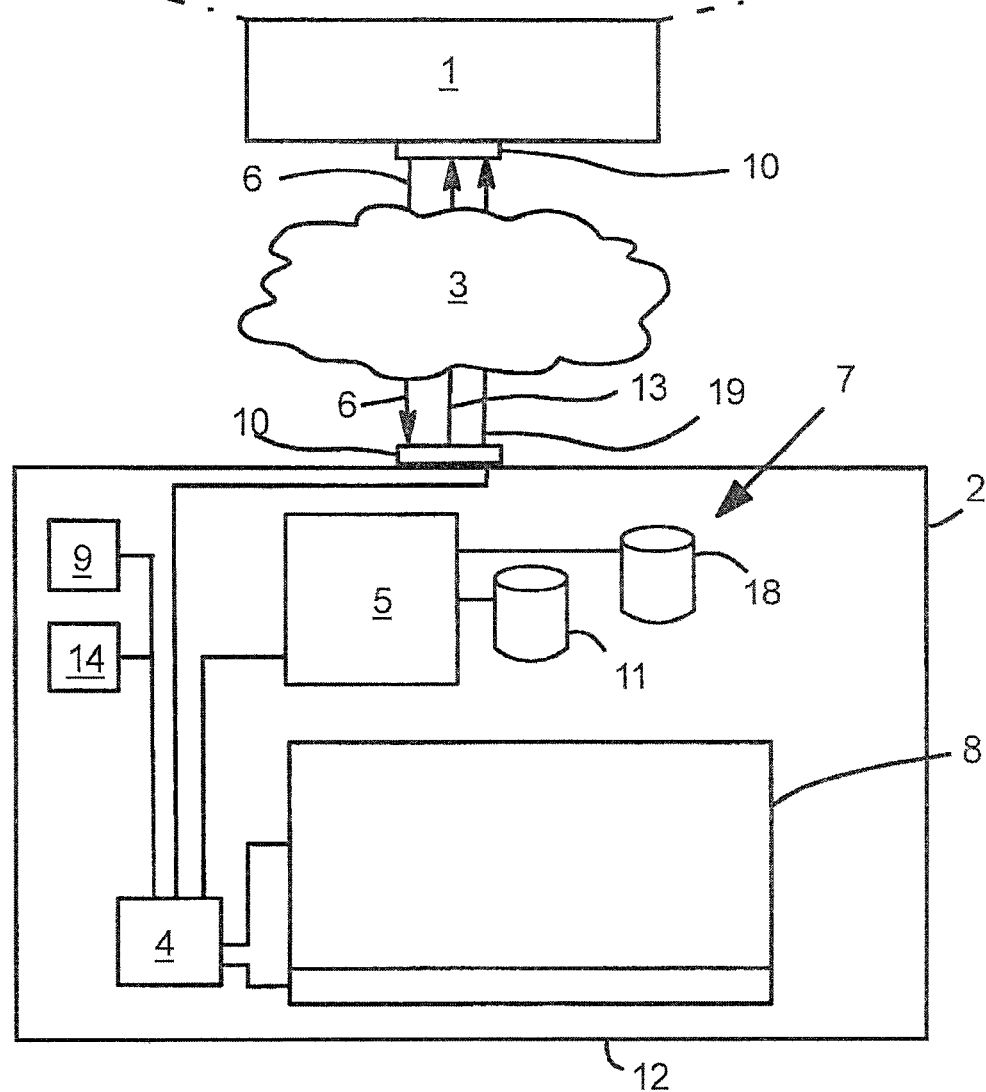

MOBILE DATA APPLIANCE FOR CHECKING MEDICATION

BACKGROUND OF THE INVENTION

Field of the Invention

The invention relates to a mobile data device for reminding patients to take medications and the like, with a power supply unit, with a computing unit for processing medication data, with a storage unit for storing medication data, with a display unit for displaying the medication data, with a signal transmitter unit for emitting a reminder signal for taking medication, and with an interface unit for external data exchange.

Description of the Related Art

A mobile data device for reminding patients to take medication is known, for example, from DE 297 12 539 U1 in which the mobile data device is integrated in a medication storage and dosing device. If the medications are not taken by the patient at a predetermined time from a receptacle compartment of the mobile data device, an alert signal is emitted optically or acoustically which prompts the patient to take the provided medication.

A mobile data device for reminding patients to take medications that is not coupled with a medication dispenser is known from DE 20 2012 000 410 U1. The mobile data device has a display unit with a display by means of which data relevant to taking medication, for example, the name of the medication and the amount to be taken, can be displayed. A signal transmitter unit ensures that a corresponding reminder signal is emitted and the patient is prompted to read the data on the display unit relevant to taking the medication. The mobile data device further has an input unit by means of which the patient can confirm that the medication has been taken. In this way, it can be determined when the medication concerned is depleted. The physician can be informed punctually via an interface unit before the medication has been entirely used up such that the physician can optionally dispense a new prescription. By being relayed to a corresponding pharmacy, the medication can be punctually supplied to the patient. The mobile data device further comprises a sensor unit with sensors for determining body-related condition data such as, for example, oxygen saturation, heart rate and the like. The interface unit (camera) comprises a visual communications interface so that it is possible to establish contact with a physician in case of questions. A disadvantage of the mobile data device is that correct input of medication data is not ensured. As a result, errors can occur which may not be noticed by the treating physician until it is too late.

Therefore, it is the object of the present invention to further develop a mobile data device for checking medication such that the taking of medication by patients is made more efficient in a simple manner.

BRIEF SUMMARY OF THE INVENTION

In order to meet this object, the invention in connection with the preamble of Claim 1 is characterized in that the storage unit has a medication plan storage in which medication data generated by an authorized entity are stored, and in that a medication plan program is provided by means of which medication data are read out of the medication plan storage in a time-dependent and/or location-dependent manner and the reminder signal is visualized via the display unit and/or emitted via the signal transmitter unit.

According to the invention, the mobile data device has a medication plan storage for which only an authorized entity such as, for example, a physician or a pharmacist, has access privileges. The medication plan storage has the medication data that are conveyed to the patient in a display unit as relevant data for the taking of medication with the prompt to take the medication. For this purpose, the mobile data device has a medication plan program which reads out the medication data stored in the medication plan storage in a time-dependent and/or location-dependent manner and supplies the medication data to the display unit or signal transmitter unit. The medication plan storage has the property that it can be read by any entity but only written by the authorized entity. Accordingly, since only the physician or the pharmacist is authorized, for example, to write into the medication plan storage, erroneous input of medication data into the mobile data device can be prevented.

According to a preferred embodiment form of the invention, the mobile data device has security means so that an external data exchange or writing into the medication plan storage can be carried out exclusively by the authorized entity. The authorized entity is the only one permitted to write into the medication plan storage. This ensures that the reminder function of the mobile data device is based on correct medication data.

According to a further development of the invention, a symmetrical or asymmetrical authentication algorithm is provided as security means by which the communication between the authorized entity on one hand and the mobile data device on the other hand is controlled. Therefore, the authorization of the data sender is always checked before the medication plan storage is written into. A key for an encryption algorithm, for example, can serve for this purpose. A challenge-response communication between a computer apparatus of the authorized entity and the mobile data device is preferably carried out before the medication data can be read into the medication plan storage. For example, the data device sends a random number to the computer apparatus which is encrypted in the computer apparatus and is then sent back to the data device. The encrypted random number that was sent is decrypted in the data device and is checked to determine whether or not this sent decrypted random number is the random number that was originally sent. If the comparison is positive, the computing unit is considered to be the authorized entity so that the corresponding medication data can be written into the medication plan storage. If the comparison is negative, the external computing unit is considered an unauthorized entity and access to the medication plan storage is blocked. Alternatively, the cryptographic security method provided for electronic health insurance cards can also be used so that the expenditure on cryptography with respect to the computer apparatus of the physician or pharmacist is reduced.

According to a further development of the invention, the mobile data device has an input unit for inputting a confirmation signal. When the medication has been taken at the times specified by the mobile data device, this can be documented in that the user actuates the input unit. In this way, the user, and optionally the physician can later monitor whether the medication is being taken correctly.

According to a further development of the invention, the mobile data device has a sensor unit for determining body-related condition data such as, for example, pulse, blood pressure and the like. The mobile data device advantageously undergoes a functional expansion in this way so that the user can utilize the mobile data device for numerous health-related tasks.

According to a further development of the invention, the mobile data device has a body condition storage which cooperates with a body monitoring program so that, after the actual body-related condition data which are determinable by means of the sensor unit are compared with reference body-related condition data which are stored in the body condition storage, information signals are generatable by means of which the user is notified about the current state of health. Alternatively or additionally, if the deviation of actual condition data from reference condition data is too great, the physician can also be notified via the interface unit so that the medication plan storage can optionally be changed in a timely manner.

According to a further development of the invention, the interface unit has a cable connection and/or a radio link and/or a card reader device. The radio link can be a LAN and/or WLAN connection which allows the physician to receive updated information about the user's state of health or to monitor the user's intake of medication. Particularly when there are deviations from the allowed medication intake or body condition data of the user, the medication plan can be quickly corrected or modified by transmitting a corresponding alarm/alert signal to the physician.

According to a further development of the invention, the mobile data device is provided with holding means so that it can be detachably attached to a body part of the user, for example, to an arm. The holding means can for example be formed as an armband so that the mobile data device is formed as a medical bracelet.

BRIEF DESCRIPTION OF THE SEVERAL VIEWS OF THE DRAWINGS

In the following, an embodiment example of the invention will be described in more detail referring to the FIGURE.

The FIGURE shows:

FIGURE a block wiring diagram of a system for controlling the correct intake of medication by a user.

DETAILED DESCRIPTION OF THE INVENTION

A system for controlling the medication intake of a patient/user substantially comprises a computer apparatus 1 of an authorized entity and a mobile data device 2 which are coupleable to one another via a communications interface 3 for a data exchange.

The computer apparatus 1 can be arranged in a doctor's office and can constitute the authorized entity based on the exclusive access by a physician. Alternatively, the computer apparatus 1 can also be arranged in a pharmacy when a pharmacist is the authorized entity.

The mobile data device 2 is formed, for example, as a medical bracelet and can be attached to a body part of a user, for example, to an elbow. As holding means for this purpose, the mobile data device 2 has the armband and a casing in which electrical components are accommodated according to FIG. 1.

The mobile data device 2 has a power supply unit 4 which can comprise a battery or a rechargeable accumulator so that the mobile data device 2 is operable independent of location.

The mobile data device 2 has a computing unit 5 for processing medication data 6, a storage unit 7 for storing data, a display device 8 for displaying data relating to the intake of medication and medication data. The computing unit 5 comprises a microprocessor or microcontroller. The storage unit 7 has a nonvolatile storage and optionally a volatile storage. The display unit 8 is formed as a liquid crystal display by means of which information is displayable in one or more colors.

The mobile device 2 further comprises a signal transmitter unit 9 for emitting a reminder signal for taking medication. In addition to this, the mobile data device 2 has an interface unit 10 for data exchange with the external computer apparatus 1.

The storage unit 7 has, on the one hand, a medication plan storage 11 in which the medication data 6 generated by the authorized entity (external computer apparatus 1) are stored. Storage and writing of medication data 6 into medication plan storage 11 is carried out exclusively by the authorized entity (external computer apparatus 1). Accordingly, only authorized persons (physician, pharmacist) are permitted to set the medication data 6 in the storage unit 7. The storage unit 7 further comprises a medication plan program which is executable in the computing unit 5 so that the medication data 6 can be read from the medication plan storage 11 in a time-dependent and/or location-dependent manner and can be displayed to the user via the display unit 8 and/or the reminder signal can be emitted for the user via the signal transmitter unit 9. The medication plan storage 11 and/or the medication plan program are preferably formed in such a way that subsequent modification of and/or addition to medication data in the medication plan storage 11 and/or program parts of the medication plan program are prevented or excluded. The medication plan program has an enablement routine which must be confirmed by the authorized entity (physician, pharmacist), namely, after the medication data 6 are written into the medication plan storage 11. The medication plan program for the patient is activated by the enable signal. If an unauthorized third party edits the medication plan program, for example, in an impermissible manner by adding medication data 6, the medication plan program would be in the deactivated state so that it would not be possible for the user to read out the medication data 6. After all, the third party would not be in possession of the authorized enable signal of the authorized entity by means of which the medication program can be activated for use by the user. The enable signal can be verified by means of an authorized signature.

The mobile data device 2 further comprises an input unit 12 which has input means so that, after taking the medication, the user can submit a confirmation signal which is stored in the storage unit 7. The confirmation signal can optionally also be further processed in the computing unit 5 or in a control unit provided for this purpose for generating a monitoring signal 13 which can be sent to the computer apparatus 1 of the authorized entity via the communications interface 3. In this way, the authorized entity (physician) is notified that the medication has been taken by the user as specified. Input means can be formed, for example, as a mechanical operating button and/or a virtual operating button integrated in the liquid crystal display.

Further, the mobile data device 2 comprises a sensor unit 14 for determining body-related condition data. For example, the sensor unit 14 can have a heart rate monitor and/or a blood pressure gauge or the like. Performance of the checking of such body-related condition data can be dictated by the authorized entity exactly as in the case of medication intake. In the case of a coronary patient, for example, the time between heart rate measurements can be specified.

Accordingly, the display unit 8 and the signal transmitter unit 9 remind the user to perform such measurement.

Security means are provided in the mobile data device 2 so that an external data exchange of data can be carried out exclusively with the authorized entity or with the computer apparatus 1 of the authorized entity. For this purpose, the mobile data device 2 has a symmetrical or asymmetrical authentication algorithm so that it can be determined by applying an encryption and/or a decryption process whether or not the mobile data device 2 communicates with the authorized computer apparatus 1. For example, a challenge-response method can be employed, wherein the computing unit 5 of the mobile data device 2 generates a random number which is transmitted via the interface unit 10 to the computer apparatus 1 of the authorized entity. This random number is encrypted in the computer apparatus 1 by means of a secret key and is then sent back to the mobile data device 2 via the communications interface 3. Since the mobile data device 2 has the same secret key as the computer apparatus 1, the encrypted random number can be decrypted with the key. By means of subsequently comparing the sent random number with the decrypted sent encrypted random number, it can be determined whether or not the computer apparatus 1 has the required authorization. If the two random numbers match, the computer apparatus 1 is authorized and a subsequent data exchange can take place. If the random number that is sent does not match the random number received, the computer apparatus 1 is unauthorized and subsequent data exchange is blocked. In the affirmative case, i.e., if the computer apparatus 1 has been determined as authorized entity, the medication data 6 collected in a medication plan 15 in the computer apparatus 1 can be transmitted from the computer apparatus 1 to the mobile data device 2 via the communications interface 3.

The medication plan 15 has been prepared by a physician. For example, the physician has prescribed a plurality of medications A, B, C and D after examining a patient. The medication plan 15 has as data, for example, a patient identification 16, the various medications A, B, C, D and associated times for taking these same medications and optionally additional information. The medication plan 15 can have a further column containing remarks concerning the respective medications. These medication data 6 have been inputted into the computer system (computer apparatus) in the doctor's office by the physician, for example, via a PC. When treatment by the physician is concluded, the patient can establish a communication link between the physician's computer apparatus 1 and the mobile data device 2, for example, by a receptionist at the reception desk of the doctor's office. For example, the mobile data device 2 can be connected to computer apparatus 1 by a cable connection. After checking authenticity—as was described above—the medication plan 15 can be transmitted from the computer apparatus 1 into the medication plan storage 11. The dialog provided to the physician to input the medication plan 15 is formed in such a way that the time-dependent and/or location-dependent input data in the mobile data device 2 can be further processed so as to be displayed in the display unit 8 in connection with times and locations corresponding to the appropriate medication A, B, C, D, or the signal transmitter unit 9 can be controlled in a corresponding manner. Accordingly, the computer apparatus 1 has a medication plan input program which allows only a determined selection of fixed time data and/or location data to be inputted.

The medication plan program can optionally be formed in such a way that after a confirmation signal is inputted by the patient which signals that a certain medication has been taken, a monitoring signal 13 is generated and transmitted via the interface unit 10 or the communications interface 3 to the computer apparatus 1 and the authorized entity. It is thus possible for the physician to check whether or not the medication has been taken.

The interface unit 10 of the mobile data device 2 can be formed in such a way that the connection to the computer apparatus 1 of the authorized entity can be carried out via a data network, for example, a LAN or WLAN network. Therefore, the communications interface 3 can comprise a radio link instead of a cable connection. The communications interface 3 can be formed, for example, as an internet network or as a mobile communications network (GSM). Alternatively, a card reader device can also be provided as the communications interface 3, and the card reader device is preferably connected to the computer apparatus 1 of the authorized entity. The mobile data device 2 has a card interface as the interface unit so that—like an electronic health insurance card—it is insertable into the card reader device. The authentication process provided for electronic health insurance cards can be used for authentication.

The mobile data device 2 can additionally have a body condition storage 18 which is connected to the computing unit 5. The body-related condition data that were measured by the sensor unit 14 are stored in the body condition storage 18. A body monitoring program can be associated with the computing unit 5. Depending on a comparison of the actual body-related condition data which were determined by the sensor unit with reference body-related condition data which were written in by the authorized entity, for example, via the medication plan 15, the body monitoring program generates an information signal 19 which is displayed in the display unit 8 and/or can be transmitted via the interface unit 10 to the computer apparatus 1 of the authorized entity. In this way, for example, the physician is notified about an elevated heart rate of the patient which can have an impact on the medication or modification of the medication plan 15.

For example, heart medications A, B, C which are to be taken by the patient at determined times and depending on boundary constraints that are noted under remarks are listed in the medication plan 15. For example, malaria tablets which would be taken depending on location, i.e., during a stay in Africa, can be listed as medication D.

The invention claimed is:

1. A mobile data device for reminding patients to take medications, with
a power supply unit (4),
a computing unit (5) for processing medication data (6),
a storage unit (7) for storing the medication data (6),
a display unit (8) for displaying the medication data (6),
a signal transmitter unit (9) for emitting a reminder signal for taking the medication, and
an interface unit (10) for external data exchange,
wherein the storage unit (7) has a medication plan memory (11) in which medication data (6) generated by an authorized entity are stored,
wherein a medication plan program is provided by means of which medication data (6) are read out of the medication plan memory (11) in at least one of a time-dependent and a location-dependent manner, and the reminder signal is at least one of (a) visualized via the display unit (8) and (b) emitted via the signal transmitter unit (9),
wherein security means are provided such that medication data (6) can be written into the medication plan memory (11) exclusively by the authorized entity (1), wherein a sensor unit (14) is provided for determining body-related condition data, wherein a body condition storage (18) is provided in which the body-related condition data are stored, and wherein a body monitoring program is provided which generates an information signal (19) depending on a comparison of actual body-related condition data with reference body-related condition data for at least one of (a) display in the display unit (8) and (b) transmitting to the authorized entity via the interface unit (10).

2. The mobile data device according to claim 1, wherein a symmetrical or asymmetrical authentication algorithm is provided as security means, wherein an authentication routine is executed by means of a key to enable writing into the medication plan memory (11).

3. The mobile data device according to claim 1, wherein that an input unit (12) is provided for inputting a confirmation signal of the patient which is further processable in the computing unit for generating a monitoring signal (13) which is sendable to the authorized entity via the interface unit (10).

4. The mobile data device according to claim 1, wherein the input means comprise at least one of a mechanical operating button and a virtual operating button integrated in the display unit (8).

5. The mobile data device according to claim 1, wherein the interface unit (10) is formed in such a way that a connection is carried out between the mobile data device (2) and a computer apparatus (1) of the authorized entity via at least one of a cable connection, a radio link and a card reader device.

6. The mobile data device according to claim 1, wherein the mobile data device (2) comprises holding means for detachable attachment to a body part of the patient.

7. A system for controlling intake of medication with a mobile data device (2) according to claim 1 and with a computer apparatus (1) of the authorized entity, wherein a medication dialog for inputting at least one of the medication plan and a medication plan input program and a key for authorization relative to the mobile data device are integrated in the computer apparatus (1).

8. A mobile data device for reminding patients to take medications, with a power supply unit (4), a computing unit (5) for processing medication data (6), a storage unit (7) for storing the medication data (6), a display unit (8) for displaying the medication data (6), a signal transmitter unit (9) for emitting a reminder signal for taking the medication, and an interface unit (10) for external data exchange, wherein the storage unit (7) has a medication plan memory (11) in which medication data (6) generated by an authorized entity are stored, wherein a medication plan program is provided by means of which medication data (6) are read out of the medication plan memory (11) in at least one of a time-dependent and a location-dependent manner, and the reminder signal is at least one of (a) visualized via the display unit (8) and (b) emitted via the signal transmitter unit (9), wherein security means are provided such that medication data (6) can be written into the medication plan memory (11) exclusively by the authorized entity (1), wherein a sensor unit (14) is provided for determining body-related condition data, wherein a body condition storage (18) is provided in which the body-related condition data are stored, and wherein a body monitoring program is provided which generates an information signal (19) depending on a comparison of actual body-related condition data with reference body-related condition data for transmitting to the authorized entity via the interface unit (10).

\* \* \* \* \*